United States Patent [19]

Steeg et al.

[11] Patent Number: 5,753,437
[45] Date of Patent: May 19, 1998

[54] METHOD OF DIAGNOSING CANCER SUSCEPTIBILITY OR METASTATIC POTENTIAL

[75] Inventors: Patricia S. Steeg, Ellicott City; Lance A. Liotta, Potomac, both of Md.; Alvaro Leone, Bari; Generoso Bevilacqua, Pisa, both of Italy

[73] Assignee: The United States of America as represented by the Department of Health & Human Services, Washington, D.C.

[21] Appl. No.: 406,005

[22] Filed: Feb. 28, 1995

(Under 37 CFR 1.47)

Related U.S. Application Data

[63] Continuation of Ser. No. 190,562, Feb. 2, 1994, abandoned, which is a continuation of Ser. No. 775,081, Oct. 11, 1991, abandoned, which is a continuation-in-part of Ser. No. 528,713, May 24, 1990, abandoned, which is a continuation-in-part of Ser. No. 107,098, Oct. 13, 1987, Pat. No. 5,049,662, said Ser. No. 775,081, is a continuation-in-part of Ser. No. 422,801, Oct. 18, 1989, abandoned.

[51] Int. Cl.⁶ .............. C12Q 1/68; C12P 19/34; C07H 21/04; C12N 15/00

[52] U.S. Cl. .............. 435/6; 435/91.1; 435/91.2; 536/23.5; 536/24.31; 935/1; 935/8; 935/77; 935/78

[58] Field of Search .............. 435/6, 7.23, 91.1, 435/91.2, 183; 436/811, 813; 536/23.1, 23.5, 24.31; 935/77, 78, 1, 8

[56] References Cited

PUBLICATIONS

Bevilacqua et al. *Cancer Research* (USA), 1989, 49/18, (5185–5190); abstract only.

*Primary Examiner*—Bradley L. Sisson
*Attorney, Agent, or Firm*—Needle & Rosenberg, PC

[57] ABSTRACT

The present invention relates, in general, to a method for diagnosing cancer susceptibility based on alterations in the nm23 gene. In particular, the present invention relates to a method of identifying individuals at risk for developing a primary cancer or at risk for suffering treatment failure, morbidity, or mortality associated with cancer. The invention further relates to a means of using genetic methods to predict individuals at increased risk for developing distant metastases.

3 Claims, 4 Drawing Sheets

FIG. 2A
BREAST

BREAST

TOTAL CASES 48
INFORMATIVE 25
ALLELIC LOSS 16 (64%)

FIG. 2B
LUNG

LUNG

TOTAL CASES 20
INFORMATIVE 12
ALLELIC LOSS 5 (42%)

FIG. 2C
KIDNEY

KIDNEY

TOTAL CASES 25
INFORMATIVE 10
ALLELIC LOSS 2 (20%)

FIG.3A    FIG.3B

COLON

| | |
|---|---|
| TOTAL CASES | 16 |
| INFORMATIVE | 9 |
| ALLELIC LOSS | 1 ⎫ |
| HOMOZYGOUS |   ⎬ 22% |
| DELETION | 1 ⎭ |

FIG.4

METHOD OF DIAGNOSING CANCER SUSCEPTIBILITY OR METASTATIC POTENTIAL

This application is a continuation of Ser. No. 08/190,562 filed Feb. 2, 1994, now abandoned, which is a continuation of Ser. No. 07/775,081 filed Oct. 11, 1991, now abandoned, which is a continuation-in-part of Ser. No. 07/528,713 filed May 24, 1990, now abandoned, which is a continuation-in-part of Ser. No. 07/107,098 filed Oct. 13, 1987, issued as U.S. Pat. No. 5,049,662 now reissued as U.S. RE 35,097; said Ser. No. 07/775,081 filed Oct. 11, 1991, which is also a continuation-in-part of Ser. No. 07/422,801 filed Oct. 18, 1989, now abandoned. The content of prior application Ser. Nos. 07/107,098, 07/422,801, and 07/528,713 are incorporated by reference.

BACKGROUND OF THE INVENTION

1. Field of the Invention

The present invention relates, in general, to a method of diagnosing cancer susceptibility and metastatic progression. In particular, the present invention relates to a method of predicting susceptibility of an individual to the development of cancer, or its metastasis comprising the use of alterations in the structure and/or expression of NM23 genes.

2. Background Information

The determination of an individual's susceptibility for the development of cancer and the metastatic spread of cancer once a primary tumor has been found are critical to the physician's choice of diagnostic and therapeutic modalities. Use of NM23 to predict metastatic spread has been limited to determination of its reduced expression at the RNA and/or protein levels (Bevelacqua et al. (1989) Cancer Res. 49:5185–5190; Hennessy et al. (1991) J. Natl. Cancer. Inst. 83:281–285; Barnes et al. (1991) Am. J. Path. 139:245–250; Hirayama et al. (1991) J. Natl. Cancner INst. 83:1249–1250).

The present invention relates to additional novel methods to predict tumor metastatic potential using NM23. It also describes the use of NM23 for predicting susceptibility to cancer development.

The murine NM23-1 (Steeg et al. (1988) J. Natl. Cancer Inst. 80:200–203)

```
GTC GCA GCC GGC GGT AAA GCC TTG TCA TCT GAA GGG GAC CAT

GGC CAA CAG TGA GCG TAC CTT CAT TGC CAT CAA GCC TGA TTC

AAG GAG CAC TAC ACT GAC CTG AAG GAC CGC CCC TTC TTT ACT

GGC CTG GTG AAA TAC ATG CAC TCA GGA CCA GTG GTT GCT ATG
                        met his ser gly pro val val ala met GTC TGG GAG GGT CTG AAT CTG GTG AAG ACA GGC CGC GTG ATG
val trp glu gly leu asn val val lys thr gly arg val met CTT GGA GAG ACC AAC CCC GCA GAC TCT AAG CCT GGG ACC ATA
leu gly glu thr asn pro ala asp ser lys pro gly thr ile CGA GGA GAC TTC TGC ATT CAA GTT GGC AGG AAC ATC ATT CAT
arg gly asp phe cys ile gln val gly arg asn ile ile his GGC AGC GAT TCT GTA AAG AGC GCA GAG AAG GAG ATC AGC TTG
gly ser asp ser val lys ser ala glu lys glu ile ser leu TGG TTT CAG CCT GAG GAG CTG GTG GAG TAC AAG AGC TGT GCG
trp phe gln pro glu glu leu val glu tyr lys ser cys ala CAG AAC TGG ATC TAT GAG TGA TAG GAC GGT GCC GGT TTT CTA
gln asn trp ile tyr glu

CCT GCT TAC TCT TGT TCT CAC AGG CAG GGG ACC AGC AAC CCT
```

-continued

```
AGA TAT TTC TGG AAC TTC TTT GAC CTG GAA GGA ACC TTT GGG

AGC CGT GAC TCC CTG TGC AGT GTT ACG TGC CAC TGT TAG ATT

AAA GTG TTT AAT CTG T POLY A
```

, human NM23-H2 (Stahl et al. (1991) Cancer Res. 51:445–449) Nucleotide sequence of the nm23-H1 and predicted protein sequence (differences with the murine nm23-H2 protein are shown)

```
TGC TGC GAA CCA CGT GGG TCC CGG GCG CGT TTC GGG TGC TGG

CGG CTG CAG CCG GAG TTC AAA CCT AAG CAG CTG GAA GGA ACC

ATG GCC AAC TGT GAG CGT ACC TTC ATT GCG ATC AAA CCA GAT
MET Ala Asn Cys Glu Arg Thr Phe Ile Ala Ile Lys Pro Asp
                                                    Ser

GGG GTC CAG CGG GGT CTT GTG GGA GAG ATT ATC AAG CGT TTT
Gly Val Gln Arg Gly Leu Val Gly Glu Ile Ile Lys Arg Phe

GAG CAG AAA GGA TTC CGC CTT GTT GGT CTG AAA TTC ATG CAA
Glu Gln Lys Gly Phe Arg Leu Val Gly Leu Lys Phe MET Gln
                                                    Leu

GCT TCC GAA GAT CTT CTC AAG GAA CAC TAC GTT GAC CTG AAG
Ala Ser Glu Asp Leu Leu Lys Glu His Tyr Val Asp Leu Lys
                                                    Thr

GAC CGT CCA TTC TTT GCC GGC CTG GTG AAA TAC ATG CAC TCA
Asp Arg Pro Phe Phe Ala Gly Leu Val Lys Tyr MET His Ser
                                                    Thr

GGG CCG GTA GTT GCC ATG GTC TGG GAG GGG CTG AAT GTG GTG
Gly Pro Val Val Ala MET Val Trp Glu Gly Leu Asn Val Val

AAG ACG GGC CGA GTC ATG CTC GGG GAG ACC AAC CCT GCA GAC
Lys Thr Gly Arg Val MET Leu Gly Glu Thr Asn Pro Ala Asp

TCC AAG CCT GGG ACC ATC CGT GGA GAC TTC TGC ATA CAA GTT
Ser Lys Pro Gly Thr Ile Arg Gly Asp Phe Cys Ile Gln Val

GGC AGG AAC ATT ATA CAT GGC AGT GAT TCT GTG GAG AGT GCA
Gly Arg Asn Ile Ile His Gly Ser Asp Ser Val Glu Ser Ala
                                                    Lys
```

-continued

```
GAG AAG GAG ATC GGC TTG TGG TTT CAC CCT GAG GAA CTG GTA
Glu Lys Glu Ile Gly Leu Trp Phe His Pro Glu Glu Leu Val
                Ser             Gln

GAT TAC ACG AGC TGT GCT CAG ACC TGG ATC TAT GAA TGA CAG
Asp Tyr Thr Ser Cys Ala Gln Asn Trp Ile Tyr Glu
Glu     Lys

GAG GGC AGA CCA CAT TGC TTT TCA CAT CCA TTT CCC CTC CTT

CCC ATG GGC AGA GGA CCA GGC TGT AGG AAA TCT AGT TAT TTA

CAG GAA CTT CAT CAT AAT TTG GAG GGA AGC TCT TGG AGC TGT

GAG TTC TCC CTG TAC AGT GTT ACC ATC CCC GAC CAT CTG ATT

AAA ATG CTT CCT CCC AGC poly A
``` and human nm23-H1 (Rosengard et al. (1989)342:177–180) Nucleotide sequence of pnm23-H2 and predicted protein nmE3H2 (differences with nm23-H1 predicted protein are shown)

```
TCT GAA GAA CAC CTG AAG CAG CAC TAC ATT GAC CTG AAA GAC
Ser Glu Glu His Leu Lys Gln His Tyr Ile Asp Leu Lys Asp
            Asp Leu         Glu         Val

CGA CCA TTC TTC CCT GGG CTG GTG AAG TAC ATG AAC TCA GGG
Arg Pro Phe Phe Pro Gly Leu Val Lys Tyr MET Asn Ser Gly
                        Ala                     His

CCG GTT GTG GCC ATG GTC TGG GAG GGG CTG AAC GTG GTG AAG
Pro Val Val Ala MET Val Trp Glu Gly Leu Asn Val Val Lys

ACA GGC CGA GTG ATG CTT GGG GAG ACC AAT CCA GCA GAT TCA
Thr Gly Arg Val MET Leu Gly Glu Thr Asn Pro Ala Asp Ser

AAG CCA GGC ACC ATT CGT GGG GAC TTC TGC ATT CAG GTT GGC
Lys Pro Gly Thr Ile Arg Gly Asp Phe Cys Ile Gln Val Gly

AGG AAC ATC ATT CAT GGC AGT GAT TCA GTA AAA AGT GCT GAA
Arg Asn Ile Ile His Gly Ser Asp Ser Val Lys Ser Ala Glu
                                                    Glu
```

-continued

```
AAA GAA ATC AGC CTA TGG TTT AAG CCT GAA GAA CTG GTT GAC

Lys Glu Ile Ser Leu Trp Phe Lys Pro Glu Glu Leu Val Asp

Gly             His

TAC AAG TCT TGT CCT CAT GAC TGG GTC TAT GAA TAA GAG GTG

Tyr Lys Ser Cys Ala His Asp Trp Val Tyr Glu

Thr         Gln Asp     Ile

GAC ACA ACA GCA GTC TCC TTC AGC ACG GCG TGG TGT CTC CCT

GGA CAC AGC TCT TCA TTC CAT TGA CTT AGA GGC AAC AGG ATT

GAT CAT TCT TTT ATA GAG CAT ATT TGC CAA TAA AGC TTT TGG

AAG CCG (poly A)
``` have been described. Other closely related members of this gene family may also exist, and provide cancer susceptibility and metastatic potential predictive information.

SUMMARY OF THE INVENTION

It is a general object of this invention to provide a method of diagnosing susceptibility of an individual to the development of cancer, and cancer metastatic potential.

It is a specific object of this invention to provide a method of diagnosing susceptibility of an individual to the development of cancer, and cancer metastatic potential based on many types of alterations to structure, expression, and/or activities of the nm23 genes.

It is a specific object of this invention to provide a method for determining a proper course of continued diagonsis and/or treatment for the above-identified individual.

Further objects and advantages of the present invention will be clear from the description that follows.

BRIEF DESCRIPTION OF THE DRAWINGS

FIG. 1. In situ hybridization of pnm23-H1 to metaphase chromosomes. Panel A. Metaphase spread containing a grain on chromosome 17 (broad arrow). Two small arrows identify nonspecific hybridization. Panel B. The same metaphase spread as shown in A after chromosome banding. Panel C. Distribution of grains on chromosome 17 in 61 metaphase spreads. Twenty-six (17.8%) of 146 total grains were present on chromosome 17 and twelve (46%) of these 26 grains were localized to the 17p11-q11 region.

FIG. 2. Allelic deletion of nm23-H1 in tumors. Southern hybridization to BglII digested human chromosomal DNA samples from: A. normal lymphocyte and breast carcinoma. B. normal lung and non-small cell lung carcinoma. C. normal kidney, kidney carcinoma and kidney carcinoma cell line. The BglII restriction digest identified two allelic bands at 7.6 and 2.3 kb. A non allelic 21 kb constant band was also evident. N: normal, T: tumor, C: tumor cell line. Numbers on the left on each panel indicate the size of the allelic bands. Arrows on the right indicate missing allele.

FIG. 3. Homozygous deletion of nm23-H1 in colon carcinoma metastasis. A. Southern hybridization of chromosomal DNA from normal colonic mucosa (N), colon carcinoma (T) and lymph node metastasis (M) to nm23-H1. B. Control southern hybridization of the same filter to human Ha-ras. The probe to Ha-ras, which maps to chromosome 11p15.5, was a 6.6 kb insert spanning the entire genomic sequence.

FIG. 4. Amplification of NM23-H1 in childhood neuroblastoma tumors of high metastatic potential. Genome DNA from normal tissue (N) and neuroblastoma tumors (T) were digested with Bgl II, and Southern blots prepared and hybridized to the pNM23-H1 CDNA insert. Lanes 1 and 2 are the matched normal and tumor DNA from one patient with Stage III neuroblastoma. Equivalent amounts of DNA were loaded onto the Southern blot. The patient is homozygous for the 2.3 kb nm23-H1 allele. The tumor DNA lane exhibits a quantitatively greater amount of hybridization to the nm23-H1 probe at the 2.3 kb allele than does the matched normal tissue, indicating nm23-H1 gene amplification in the tumor. A similar trend is observed in the second set of matched normal and tumor DNAs from a Stage III patient. Amplification of the 7.6 kb nm23-H1 band is observable. Lack of amplification would be indicated by equal intensity of hybridization to the nm23 probe in the normal and tumor lanes.

DETAILED DESCRIPTION OF THE INVENTION

The present invention relates to genetic testing for cancer susceptibility, diagnosis and prognosis. The present invention makes use of the marker for the nm23 genes, for which the human pNM23-H1 and pNM23-H2, and murine pNM23 and pNM23-1 recombinant cDNA clones have been described (Steeg, P. S., et al. (1988) J. Natl. Cancer Inst. 80:200–203; Rosengard, A. M., et al. (1989) Nature 342:177–180; Stahl, J. A. et al. (1991) Cancer Res. 51:445–449). The genetic marker itself can be a whole gene, a fragment thereof, a genomic or CDNA clone, an adjacent region, a cross-hybridizing clone, or a regulatory region thereof. The purpose of this invention is to provide novel genetic methods for the detection of (a) susceptibility to cancer and (b) cancer tumorigenic and metastatic potential.

These methods are based on (a) structural and sequence evaluation of nm23 DNA and; (b) evaluation of novel nm23 expression patterns, either at the RNA, mRNA and/or protein levels. Such information is critical to the physician's selection of diagnostic and therapeutic regimens for the patient, both prior to the development of cancer, and during cancer detection and treatment.

The present invention is based on the observation that cancer metastasis are correlated with a variety of alterations to the nm23 genes.

Structural alterations can include amplification, deletion, and point mutations of the coding and/or regulatory regions. Expression alterations include increased expression of NM23 in tumors and heterogeneous expression in tumors.

In one embodiment, the present invention relates to a method of identifying an individual at an increased risk for developing cancer metastases (for example, an individual who has had colorectal cancer, breast cancer, lung cancer, and/or kidney cancer, or any other cancer in which allelic deletion has been described) comprising:

analysing an nm23 gene of said individual for a structural alteration;

classifying an individual having a structural alteration in an nm23 gene as having an increased risk for developing cancer or cancer metastases.

The locus can be analysed by Southern blot analysis, polymerase chain reaction analysis, identification of cloned material, single strand conformational polymorphism (SSCP), or by DNA sequencing of the locus.

Examples of types of structual alterations that can be detected include but should not be limited to amplifications, deletions and point mutations. Applicants have provided the first evidence that all deletions at the nm23-H1 locus may have prognostic significance in colorectal carcinoma. Eight of 11 patients with nm23-H1 allelic deletions developed distant metastases, including 2 with TNM (TNM is the traditional method of classifying tumors based on the tumor, lymph nodes and metastases.) stage 1 lesions at initial operation (Table 2). In contrast, only 2 of 10 patients in whom nm23-H1 deletions were not detected developed distant metastases (p<0.03); no stage 1 or 2 tumor without nm23-H1 deletion has detectable distant metastasis (Table 2). Compared to patients with nm23-H1 deletions, patients without nm23-H1 deletions were evenly matched for TNM stage, follow-up time, and location of primary tumor, eliminating 3 variables likely to confound an association of distant metastases with nm23-H1 deletions of tumor DNA.

Figure 4:
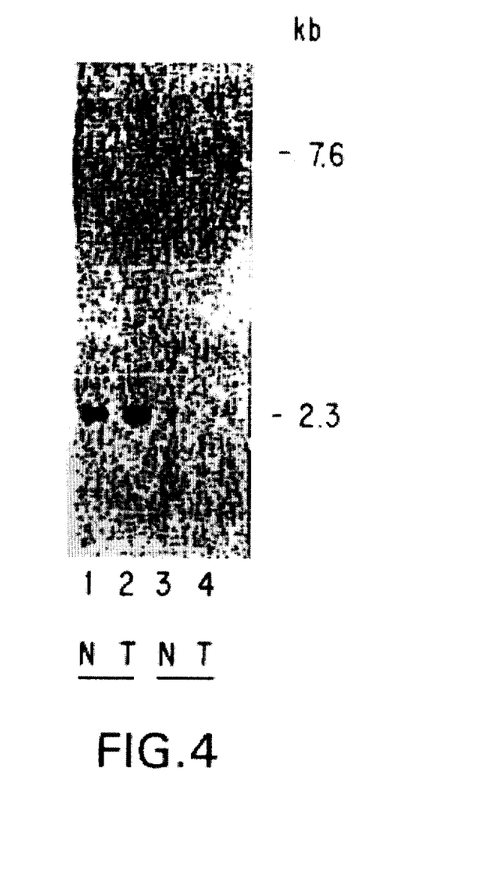

A second example is amplification of NM23-H1 allele in 10 neuroblastomas of high tumor metastatic potential (Stage III & IV) (FIG. 4).

Analysis of nm23 structural and/or regularatory sequences for point mutations can identify an individual at increased risk for the development of cancer (as in early onset familial breast cancer) or at increased risk for development of metastasis (any cancer type). The colocalization of nm23 genes with the early onset, familial breast cancer locus (Hall et al. (1990) Science 250:1684–1689) also permits Southern blot analysis of nm23 alleles in family pedigrees to be examined for cancer susceptibility.

In another embodiment, the present invention relates to a method of identifying an individual at an increased risk for developing cancer or cancer metastases comprising:

measuring the level of expression of an nm23 gene in a sample from said individual (the expression is may be measured by analysis of gene product or by analysis of mRNA transcription) and classifying an individual having an altered level of expression of an nm23 gene (ie. higher or lower than corresponding normal tissue; higher or lower than that of tumors of known low metastatic potential) relative to a reference level characteristic of a normal gene as being more likely to develop cancer or cancer metastases.

Altered nm23 expression (at the RNA, mRNA and/or protein levels) can be used to identify individuals at increased risk for the development of metastasis, as in childhood neuroblastoma.

In a further embodiment, the present invention relates to a method of identifying an individual at an increased risk for developing cancer or cancer metastases comprising:

measuring the level of protein translated from a nm23 gene in a sample from said individual and classifying an individual having an altered level of protein (preferably, at least by a factor of 2.0 higher or decreased by a factor of ½) from a nm23 gene relative to a reference level characteristic of a normal gene as being more likely to develop cancer or cancer metastases.

In yet another embodiment, the present invention relates to a method for determining a proper course of treatment for a patient suffering from cancer or cancer metastases comprising:

analysing an nm23 gene of said patient for a structural alteration;

identifying a patient having a structural alteration in an nm23 gene, which patients may require treatment proper for patients having a lesser chance of survival or decreased time to relapse; and identifying a patient lacking a structural alteration in an nm23 gene, which patients may require treatment proper for patients having a greater chance of survival and being less likely to suffer disease relapse.

In a further embodiment, the present invention relates to a method for determining a proper course of treatment for a patient suffering from cancer or cancer metastases comprising:

measuring the level of expression of an nm23 gene in a sample from said patient;

identifying a patient having an altered structure and level of expression of an nm23 gene relative to a reference level characteristic of a normal gene, which patients may require treatment proper for patients having a lesser chance of survival or decreased time to relapse; and identifying a patient having an unaltered structure and level of expression of an nm23 gene relative to a reference level characteristic of a normal gene, which patients may require treatment proper for patients having a greater chance of survival and being less likely to suffer disease relapse.

In another embodiment, the present invention relates to a method for determining a proper course of treatment for a patient suffering from cancer or cancer metastases comprising:

measuring the level of nm23 protein in a sample from said patient;

identifying a patient having an altered level of said protein relative to a reference level, which patients may require treatment proper for patients having a lesser chance of survival or decreased time to relapse; and identifying a patient having an unaltered level of said protein relative to a reference level, which patients may require treatment proper for patients having a greater chance of survival and being less likely to suffer disease relapse.

The present invention is described in further detail in the following non-limiting examples.

EXAMPLES

The following protocols and experimental details are referenced in the examples that follow:

Isolation of nm23-H1 and nm23-H2 CDNA.

Two distinct cDNAs were isolated form a CDNA library made form normal human fibroblast mRNA. Standard techniques were used throughout. As a probe, we used the 502 base HpaII restriction fragment of pnm23-M1. Steeg, et al. This DNA was isolated from agarose gel electrophoretograns using DE45 membrane (Schlicher and Schuell). The DNA was made radioactive using the nick translation reaction (Amersham kit) and p32PdCTP (Amersham). The individual bacteria of the CDNA library, obtained from Hiroto Okayama, (Okayama, et al.) was dispersed on agarose luria broth plates. Following growth they were transferred to nitrocellulose (Schlicher and Schuell), lysed using 0.5M NaOH and 1.5M NaCl, and neutralized in 1M NH Ac. DNA was fixed to the nitrocellulose by baking. Hybridization with the radioactive probe was conducted in 40% formamide, 0.75M NaCl, 0.075M Na citrate, 0.2% Bovine Serum Albumen, 0.2% Ficol, and 0.2% polyvinyl pyrolidone, and 2 mg/ml DNA. Hybridization was conducted for 15 hours at 42° C. Following hybridization, the filter was washed twice with 0.3M NaCl, 0.03M Na citrate, at room temperature for 20 minutes followed by two wastes at 42° C. in 0.015M NaCl and 0.0015M Na citrate for 20 minutes each. Positive hybridization was detected for 5 bacterial by autoradiography. These were purified by single cell cloning.

DNA was extracted from each of the five clones and analyzed by restriction enzyme analysis. A distinct pattern was identified for two clones, pnm23-H1 and pnm23-H2. These were subjected to further analysis.

The DNA sequence of pnm23-H1 and pnm23-H2 was determined using the dideoxy chain termination method (U.S. Biochemical kit). For this purpose, the XhoI fragment of pnm2-H1 and pnm23-H2 was removed from the plasmid and inserted using standard techniques into the Sal I site of M13mpl8 (BRL). DNA sequence analysis was conducted using synthetic 17 base oligonucleotides as reaction primers. The DNA sequence of pnm23-H1 and pnm23-H2 (shown above) shows that pnm23-H1 contains nucleotide sequence upstream of the putative translation initiation codon (nucleotide 87), and indicates that pnm23-H2 contains a partial copy of a mRNA beginning within the open reading frame. The non-identity of nucleotide sequence (94% similarity) indicates that pnm23-H1 and pnm23-H2 are the products of separate genes.

Production of nm23-H1 and nm23-H2 Protein.

The nucleotide sequence of pnm23-H1 and H2 can be translated into a predicted protein sequence for the corresponding proteins. Several methods can be used to generate such protein.

(1) Standard chemical procedures can be used to synthesize peptides corresponding to all or a portion of the nm23-H1 or H2 amino acid sequence. These peptides can be coupled to carrier proteins such as KLH for antibody production.

(2) Protein corresponding to all or part of nm23-H1 or part of nm23-H2 can be synthesized in bacteria under the direction of bacterial transcription promotion signals. The nm23-H1 protein has been expressed under direction of the bacteriophage lambda PL promoter in a vector similar to others described. The plasmid pBR322 was digested with EcoRI and AuaI and the base fragment isolated by agarose gel electrophoresis. This was mixed with a synthetic restriction fragment containing several enzyme sites, a bacterial ribosome binding site and a translation initiation codon containing a NcoI restriction enzyme site. These were reacted with T4 DNA ligase transformed into E. coli and plasmids of correct structure identified. DNA from these plasmids were digested with BstXI and BamHI and mixed with a BstXI-BglII digestion of the 4.5 kb Hind III fragment of bacteriophage DNA. This BstXI-BglII fragment contains the PL promoter. Following ligation and transformation into E. coli (which contains a cI 857 prophage) plasmids were identified. DNA from these plasmids was digested with BstXI and HpaI and the cohesive ends of each DNA filled in by E. coli DNA polymerase I large fragment. This was ligated using standard conditions and transformed into E. coli. The nm23-H1 was removed from M13mp18 by digesting with NcoI at a ratio of 1 unit of enzyme per 1 μg DNA for 2 minutes to produce partially digested molecules as verified by the conversion of supercoiled molecules to linear forms. This was phenol/$CHCl_2$ extracted and ethanol precipitated to remove NcoI enzyme and further digested with EcoRI. The 0.7 kb fragment was isolated from agarose gel electrophoretograms. These fragments were combined with plasmid pPL which had been digested with EcoRI and NcoI ligated and transformed into E. coli.

Bacterial clones were identified which could direct the synthesis of human nm23-H1 protein. Bacteria were grown to OD 660=1 at 32° C. and temperature shifted to growth at 42° C. for 16 hours. Total bacterial protein was examined by electrophoresis in containing 15% polyacrylamide gels containing SDS. The human nm23-H1 protein was identified as a 19 kDa protein, capable of reacting with anti-peptide antisera directed against amino acids 86 to 102 of the protein.

The human nm23-H1 protein can be purified from the bacteria by a variety of methods. For example, following growth and temperature shift induction bacteria were lysed by sonication in 20 mM Tris pH 7.5 150 nM NaCl (TBS). Insoluble material was removed by centrifugation at 100,000 xg for 30 minutes. Ammonium sulfate was then added to 60% saturated solution and proteins allowed to precipitate at 4° C. for 10 minutes. These proteins were collected by centrifugation at 100,000 xg for 10 minutes and the precipitate dissolved in TBS. Following dialysis for 716 hours, a fine precipitate is collected by centrifugation at 10,000 xg for 10 minutes. This is made soluble in TBS and 1 mM DTT. Protein prepared in this way is more than 80% pure as judged by SDS polyacrylamide gel electrophoresis. Protein prepared in this way is suitable for use as an immunizing antigen in antibody production and in biological modification experiments.

The nucleotide sequence of nm23-H1 and H2 allow the expression of either protein in eucaryotic cells. There are a variety of systems available for expression of proteins in cells ranging from yeast to human tissue culture cells. The essential elements required for expression of nm23-H1 or H2 protein was nucleotide sequences capable of directing synthesis of the nm23.

Production of nm23 antibody.

The products described in the above section can be used as antigens. These can be used intact or following coupling to a carrier protein such as Keyhole Limpet hemocyanin. Coupling can be conducted using established techniques and using such crosslinking agents as EDC. The antigen is then mixed with adjuvant (e.g., Freund's) and injected into the animal (such as rabbit, rat, or goat). Following booster injections with antigen mixed with adjuvant (e.g., Freunds incomplete) the animal is bled and sera prepared. The presence of antibody can be monitored by immunoprecipitation, western blot, or solid phase binding assay (e.g., ELISA). Polyclonal antisera to nm23-H1 or H2 can be prepared in purified form by affinity chromatography. The immunoglobulin molecules can be obtained from the sera by staphylococcal protein A binding and anti-nm23-H1 or H2 obtained by binding to a solid matrix to which the appropriate nm23 antigen has been chemically fixed.

Preparation of Monoclonal Antibody.

Balb/c mice were made immune by 3 IP injections of 100 ug purified nm23-H1 protein of 1 week intervals mixed with Freund's complete adjuvant for the immunization and Freund's incomplete adjuvant for the boosters. Hybridomas were prepared by the method of Lane et al. Methods in Enz. 121, p. 183 (1986). The fusion partner was the myeloma P3x63 - Ag8.653 obtained from ATCC. Fused cells were plated with intraperitoneal cells obtained by the method of Lane, et al. , *Hybridoma*, Vol. 7 p. 289 (1988). Hybridomas were grown in DMEM supplemented with NCTC-109 (Gibco) 7.5% Fetal Bovine Serum (Sigma) 7.5% CSPR-3 (Sigma) 1 mM Na pyruvate, 100 units Penicillin, 100 ug streptomycin, 10 ug/ml insulin, and 25 uM B-mercapto ethanol, containing 0.1 mM hypoxanthine, 0.4 uM amhopterin, and 0.016 mM Thymidine. Hybridoma clones were grown in 96 well dishes for two weeks. Anti-nm23 producing hybridomas were identified by ELISA. Purified nm23-H1 protein was attached to Immulon 1 dishes and hybridoma culture media were allowed to react for 2 hours at room temperature. Antibody reaction was detected using biotinylated goat antimouse antibodies and steptavicdin horseradish peroxidase using the conditions in the BRL HyBRL kit. Positive hybridomas were cloned by limiting dilution in the above media containing 5% hybridoma growth supplement (Fisher). These were tested for reactivity in ELISA. Reaction with human nm23 protein was confirmed by a Western blotting assay.

Detection of Metastatic Tumors.

Antibodies specific for the human nm23-H1 and H2 proteins can be made as described. One such antibody directed against amino acids 45 to 61 of the nm23-H1 sequence was used to detect nm23 protein in tumor sections. Standard techniques can be used for the preparation of sections for immunohistochemistry. These methods include frozen sections or formalin fixation of the sample followed by paraffin embedding. In this example, tumor sections were fixed overnight in 10% neutral buffered formalin and embedded in paraffin using an automatic tissue processor (Fisher). Five micron sections were cut and deparaffinized using standard procedures involving xylenes and alcohol. Sections were then immunostained using affinity purified anti-peptide antibody at 1/200 dilution: Immunostaining was done using standard techniques as provided by the manufacturer (Vector) using biotinylated goat antirabbit antibody followed by avidin biotinylated horse radish peroxidase. The color reaction (diamino benzidine tetrahydro chloride) at 0.5 mg/ml for 5 minutes at room temperature was followed by a water wash to stop reaction. Sections were then counter stained using Mayers hematoxylin, dehydrated and coverslips applied using standard methods. Sections were then examined by light microscopy for distinct cytoplasmic staining. Two samples from breast cancer patients where tumor had spread to the axillary lymph nodes show little staining; two samples from patients with cancer confined to the breast show distinct staining. This indicates that detection of low nm23 protein expression identifies malignant tumors with a propensity to spread outside the primary site.

Identification and structural Form of the NM23 Gene.

A murine cDNA clone for the NM23 gene was identified by differential screening of a murine melanoma cDNA library. Total cellular RNA was extracted from the K1735 murine melanoma TK-Eve cell line obtained as reported in Chemical and Experimental Metastasis (1987) and poly A-containing sequences isolated. Double-stranded cDNA was prepared from this RNA and was inserted into the Pst I site pBR322 plasmid by G/C tailing. RRI bacteria were transformed with the recombinant plasmids to generate a 40,000 component cDNA library. All techniques employed were those which are standard in the art to which this invention belongs and are well known to one of ordinary skill in the art. The recombinant plasmid thus obtained was designated pNM23.

The pNM23 cDNA clone was selected on the basis of differential hybridization of RNAs from low and high metastatic cell lines. Duplicate filters of the cDNA library were prepared: One set of filters was hybridized to $^{32}$P-labelled poly A+ RNA from the K1735 murine melanoma TK-Eve cell line, which is highly metastatic: the duplication set of. filters was hybridized to $^{32}$P-labelled RNA from the K1735 murine melanoma Clone 19 cell line, which is of low metastatic potential. Clones exhibiting differential hybridization to these two probes were tested for their pattern of hybridization to RNAs from seven K1735 murine melanoma cell lines of varying metastatic potentials. In these experiments, the cDNA inserts were purified, radiolabelled, and hybridized to Northern blots containing RNA from seven K1735 cell lines. The hybridization pattern of the pNM23 cDNA clone to each of the K1735 RNAs was inversely correlated with their experimental and spontaneous metastatic potentials.

The pNM32 cDNA clone contains a 250 bp insert. The DNA sequence was determined by using standard dideoxy and Maxam-Gilbert methods. The cDNA insert was radiolabelled and used to screen a murine fibroblast cDNA library to obtain a longer cDNA clone and its DNA sequence is shown above. Computer analysis of the 3' 600 bp of this clone against Genebank animal, bacterial and viral sequences indicates that the NM23 is a novel, heretofore uncharacterized gene.

The murine NM23 gene is present as one band of EcoRI digested murine chromosomal DNA, each approximately 6 kb in length, on Southern blots.

A deposit of NM23 has been made at the ATCC, Rockville, Md. on Oct. 7, 1987 under the accession number 67539. The deposit shall be viably maintained, replacing if it becomes non-viable during the life of the patent, for a period of 30 years from the date of the deposit, or for 5 years from the last date of request for a sample of the deposit, whichever is longer and, upon issuance of the patent, made available to the public without restriction in accordance with the provisions of the law. The Commissioner of Patents and Trademarks, upon request, shall have access to the deposit.

Utility of the NM23 Gene.

Hybridization of the cDNA clone for the NM23 gene to cellular RNA has predicted metastatic potential in both animal experimental metastasis model systems and human cancer. In each case, NM23 RNA levels were greatest in cells and tumors of low metastatic potential, and declined in highly metastatic specimens. NM23 expression is not related to immunologic phenotype.

Four animal experimental metastasis model systems have been employed. In the K1735 mouse melanoma system, seven cell lines derived from a single K1735 melanoma are available. The metastatic potential of these cell lines was determined by both i.v. injection of cells into the tail vein of mice (experimental metastasis) and s.c. inoculation of cells (spontaneous metastasis). The experimental metastatic potentials of the K1735 cell lines are significantly different; spontaneous metastatic potential paralleled experimental metastatic potential. Five µg of total cellular RNA was electrophoresed in a formaldehyde containing agarose gel and transferred to a Northern blot: the blot was hybridized to $^{32}$P-nick translated cDNA insert from the pNM23 cDNA clone. NM23 RNA levels are approximately ten-fold higher in the two low metastatic K1735 cell lines (Clone 16 and Clone 19) than in five related highly metastatic K1735 cell lines (M2, M4, TK, TK-Eve and TK-Liver).

Hybridization data in a rat nitrosomethylurea (NMU) induced-mammary carcinoma model system provided further evidence of the diagnostic potential of NM23 gene. A single injection of NMU in Buffalo rats induced mammary carcinomas, 90% of which are nonmetastatic for periods of up to one year; NMU-induced metastatic carcinomas remain metastatic upon passage. Total cellular RNA was extracted from three types of NMU tumors: nonmetastatic mammary carcinomas, metastatic mammary carcinomas, and pulmonary metastases. RNA was applied to a slot blot and hybridized to the cDNA insert of the pNM23 cDNA clone. Average NM23 RNA levels were found to be highest in nonmetastatic NMU tumors, i.e., 170% higher than metastatic mammary carcinomas and 320% higher than in pulmonary metastases. Variability observed in NM23 RNA levels within each type of tumor may reflect quantitative differences in metastatic potential which exist within a qualitative grouping.

Hybridization of the cDNA clone for the NM23 gene was also tested in murine mammary tumors of varying metastatic potentials. Balb/c mice carrying either the RIII or C3H strains of mouse mammary tumor virus (MMTV) develop mammary tumors which are of low and high metastatic potential, respectively. Total cellular RNA was extracted from mammary tumors in Balb/cf.RIII and Balb/cf.C3H mice, and NM23 RNA levels determined by Northern blot analysis using the BamHI-Pst I restriction fragment of pNM23-1 as a probe. NM23 RNA levels were 3.5-fold greater in low metastatic Blab/cf.RIII mammary tumors than in high metastatic Balb/cf.C3H tumors.

Rat embryo fibroblasts (REF) have been transfected with either ras or ras+adenovirus Ela genes: the ras transfected cells have significantly greater experimental metastatic potential than ras+Ela transfected cells. Average NM23 RNA levels of ras+Ela transfected REF are three-fold greater than those of ras transfected cells (FIG. 6). These data were confirmed by in situ hybridization of the pNM23 cDNA insert to ras or ras+Ela transfected cells: average cellular RNA in ras+Ela REF were significantly higher than in ras REF.

In summary, NM23 RNA levels were higher in less metastatic cells and tumors than in highly metastatic specimens in four animal metastases model systems. An advantage of the animal experiments is the availability of closely related specimens that differ in very few parameters, one of which is metastatic potential. Differential hybridization of pNM23 cDNA clones has been demonstrated both in vitro and in vivo and to several types of cancers employing different methods to confirm the data.

NM23 RNA levels were also found to be differentially expressed in human cancer tissues. In the study, NM23 RNA levels in breast carcinoma surgical specimens were determined by in situ hybridization. Human primary breast cancer (infiltrating ductal carcinoma) samples were obtained at mastectomy including axillary lymph node dissection. The level of NM23 RNA expression in a given tumor was compared to the number of axillary lymph nodes positive for metastases in the same patient. As shown, significant differences in the hybridization intensity of the pNM23 cDNA insert were observed. Comparison of NM23 levels and traditional indicators of metastatic potential indicate the diagnostic potential of this gene: a correlation coefficient of −0.8 was obtained between the number of positive axillary lymph nodes and NM23 RNA levels. NM23 levels have also been found to be differentially expressed in human colon carcinomas (data not shown).

It is clear from the results presented herein that NM23 gene or a portion thereof can be employed for hybridization with tumor RNA to determine the tumor NM23 RNA levels and thus predict metastatic potential.

The NM23 gene can be produced in volumes suitable for commercial use. The pNM23-1 cDNA can be grown in large quantities by the alkaline lysis plasmid preparation method described below. Alternately, NM23 cDNA or genomic fragments from any species can be cut with a restriction enzyme to obtain a specific DNA sequence on the 3' and 5' ends and ligated into other vectors with the compatible restriction site. Such vectors include, but are not limited to, viral phages or bacterial plasmids.

The pNM23-1 plasmid can be inoculated into large cultures of LB Broth containing 50 µg/ml ampicillin, grown to an OD 650=0.6, and incubated overnight in 20 µg/ml of chloramphenicol. The bacteria are pelleted by centrifugation, resuspended in 50 mM Glucose, 10 mM EDTA, 25 mM Tris, pH 8. Lysozyme is added to a final concentration of 40 mg/ml, and incubated on ice for 30 minutes. Two volume of a solution of 0.2M NaOH, 1% (w/v) SDS are added on ice, and the mixture incubated for 10 minutes. Lysis is completed by adding 0.5 volumes of a solution of 3M potassium acetate, 1.8M Formic Acid, and incubating on ice for 30 minutes. The bacterial debris is pelleted by centrifugation. DNA in the supernatant is precipitated by adding 0.6 volume of Isopropanol, incubating at room temperature (22°–24° C.) for 15 minutes, and pelleting the DNA by centrifugation. The DNA is resuspended in mTE (50 mM Tris, pH 8, 10 mM EDTA), and made 1.55 g/ml CsCl and 0.6 mg/ml Ethidium bromide. The solution is sealed in ultracentrifuge tubes and centrifuged in a Ti50 rotor at 45,000 rpm for 36 hours, or under similar conditions in other rotors. The plasmid DNA is removed from the tube using a needle and syringe under ultraviolet light, resealed and centrifuged under similar conditions. The plasmid DNA band is again removed from the ultracentrifuge tube using a needle and syringe, extracted with water-saturated butanol, and diluted with four volumes of water. The DNA is precipitated by adding 1:20 volume of 4M NaAcetate, pH 5, and 2 volumes of ethanol, freezing until solidified, and pelleting by centrifugation. The DNA is resuspended in mTE, phenol and chloroform extracted, and ethanol precipitated. The final DNA pellet is resuspended in water. Of course, alternate methods of plasmid preparation may also be utilized.

The pNM23-1 cDNA insert can be purified from the plasmid by restriction endonuclease digestion, with BamHI and PstI, or other enzymes. The cleaved DNA can be separated electrophoretically on either low melting temperature agarose or acrylamide gels. The cDNA insert can be stained in ethidium bromide and visualized under ultraviolet light. The plasmid band is cut out. From agarose gels, the DNA band can be melted, phenol extracted and used. Other methods well known to one of ordinary skill in the art may also be used to purify cDNA inserts as well.

The cDNA insert can be radiolabelled by various means. Most common is a nick-translation, in which DNA is incubated in 50 mM Tris, pH 7.2, 10 mM $MgSO_4$, 0.1 mM dithiothreitol, 0.02 mM each deoxynucleotide, alpha-$^{32}$P-labelled deoxynucleotide, DNase I and DNA Polymerase I at 15° C. for one hour. The DNA is separated from unincorporated nucleotides by gel filtration chromatography.

Total cellular RNA can be extracted using guanidine hydrochloride, guanidine isothiocyanate or other methods. The tumor is pulverized in a frozen mortar until it is a fine powder. It is suspended in 4M guanidine isothiocyanate, 2.5 mM sodium acetate, pH 6, 0.835% (v/v) beta-mercaptoethanol (GIT Buffer), and the cells broken open in a Dounce homogenizer. DNA is sheared by passing the solution through a syringe with an 18-gauge needle. An ultracentrifuge tube is loaded with a cushion of GIT buffer containing 5.7M CsCl. The cell lysate in GIT buffer is overlaid, and the tube filled with GIT buffer. The tube is centrifuged at 175,000 X g, overnight. The RNA is harvested from the bottom of the ultracentrifuge tube, in 10 mM Tris, pH 7.5, extracted with phenol and chloroform, and ethanol precipitated as previously described. The RNA pellet is resuspended in water and stored at −20° C.

Tumor NM23 RNA levels can be determined by any suitable method, two examples of which are illustrated:

(1) RNA levels for NM23 can be determined by Northern blot hybridization. A 1.0% agarose gel containing MOPS (20 mM 3-(K-morpholino) propanesulfonic acid, 5 mM sodium acetate, 1 mM EDTA) and 0.0199% (v/v) formaldehyde (0.054 volume of 97% formaldehyde) is poured in a fume hood, adding the formaldehyde only after the solution has cooled. Ethanol precipitated RNA is resuspended in RNA loading buffer (0.72 ml formamide, 0.16 ml 10XMOPS, 0.26 ml 37% formaldehyde, 0.18 ml water, 0.1 ml 80% glycerol, 0.08 ml saturated bromophenol blue) and is heat-denatured for 15 minutes at 65° C. The samples are loaded onto the gel and electrophoresed in MOPS. The gel is washed for one hour in three changes of 20xSSC (3M NaCl, 0.3M Na citrate, pH 7), and the RNA is eluted onto a nitrocellulose blot by capillary action, using 20xSSC. The nitrocellulose blot is washed in 2XSSC and baked at 60° C. in a vacuum oven. The blot is prehybridized in 5xSSC, 0.1% (w/v) SDS, 1xDenhardt's solution, 50% (v/v) formamide, 100 mM Tris, pH 7.5, 0.25 mg/ml freshly boiled Salmon sperm DNA, 10% (w/v) Dextran sulphate for at least three hours in a 37° C. water bath. Boiled radiolabelled NM23-1 CDNA insert is added at $10^6$ CPM/ml, and hybridized overnight at 37° C. The blot is washed sequentially in 2, 1, 0.5 and 0.25xSSC, 0.1% SDS (w/v), 1 mM EDTA at 55° C., and exposed to X-ray film. NM23 RNA levels can be quantitated by densitometry or other means. Other methods for determining NM23 RNA levels, such as slot blots, RNase protection or dot blots, may also be used.

(2) An alternate method for determining NM23 RNA levels is in situ hybridization. Paraffin embedded sections of tumors are placed on poly-lysine coated microscopic slides, deparaffinized in xylene, hydrated by incubation in decreasing amounts of ethanol (100% to 20% v/v), incubated in 5 micrograms Proteinase K in 10 mM Tris, pH 7.5, and in phosphate buffered saline. The sections are incubated in the same prehybridization mixture used for Northern blot hybridization and $2\times10^6$ CPM/slide or radiolabelled NM23 probe added in prehybridization mixture. The slides are hybridized overnight at 37° C. in a humidified atmosphere and washed in 2 and 1XSSC, 50% formamide (v/v) at 37° C. The slides are dried in increasing concentrations of ethanol (20% to 100%, v/v). The slides are dipped in photographic emulsion dried in the dark, and stored at 4° C., until processing by immersion in photographic developer. Slides can be counterstained with any dye. Other in situ hybridization protocols may be used as well to incorporate riboprobes, biotin or other nonradioactive labelled probes and like well known to one of ordinary skill in the art.

Prediction of metastatic potential from NM23 RNA levels comprises comparison of tumor NM23 levels with reference standards for the tumor type under consideration. Optimally, reference standard RNA levels are determined as side-by-side controls in the NM23 assay to control day-to-day variations of techniques and reagents. The quantitation of NM23 RNA levels and comparison to standards can be performed either by lab personnel or by automated systems.

The diagnostic kit comprises at least a container containing NM23 gene, either in whole (for example, 730 bp long) or in part (for example, 230 bp fragment) or inserted into a vector. The gene could be made available either in a lyophilized or a buffered medium. For longer self-life, the contents of the container could be cryopreserved. The kit may also include instructions for performing the assay to determine NM23 levels in a cell or tissue sample.

In is clear of course, that given the nucleotide sequence of NM23, the same is readily synthesized by commercially available synthesizer equipments and such synthesized product then used in accordance with the present invention.

THERAPEUTIC APPLICATION OF NM23 GENE AND ITS ENCODED PROTEIN

The therapeutic potential of the NM23 gene was tested by transfecting a murine NM23-1 cDNA into high metastatic potential K-135 TK melanoma cells. Of course this in only one way of elevating the NM23 functional activity in cells and other methods will be easily suggested to one of ordinary skill in the art. The transfection enabled increased expression of the NM23 gene in TK cells observable by a NM23-1 RNA transcript of a unique size on Northern blots and by increased total 17 kDa NM23 protein levels. In the results shown in FIG. 10 NM23-1 transfectants were randomly chosen and compared to control transfected lines from the same transfection. In the results shown in FIGS. 11 and 12 stable, high NM23-1 expressing TK lines were selected and characterized as compared to randomly chosen control lines. In both cases, the NM23-1 transfectants produced less pulmonary metastases than the control transfectants. Expression of the NM23-1 cDNA, therefore, reduced metastatic potential. A reduced incidence of primary tumor formation was also noted in the NM23-1 transfectants indicating the usefulness of NM23 in the treatments or controlling the activities of primary tumors.

The NM23-1 cDNA clone, either in whole or in part, can also be utilized for cancer therapy. The NM23 protein sequence is virtually similar in all species, NM23 cDNAs or genomic DNAs from nay species, or NM23 homologues can, of course, also be similarly used. The NM23 protein or a part of it from any species can also be employed for therapeutic purposes.

One form of cancer therapy would involve increasing the amount of NM23 expression in tumor cells to make primary tumors less aggressive and reduce metastasis. NM23 DNA could be placed in a viral or other expression vector and targeted to cancer cells in gene therapy by techniques well known to one of ordinary skilled in the art. NM23 could also be similarly expressed in a host endothelial or any other cell to produce large quantities of the protein in the bloodstream. In this case the NM23 expression vector could be transfected in vivo into normal cells taken from the patient. The transfected cells could then be reintroduced into the patient. The DNA could be used as is or modified by standard techniques. Modifications include encapsulation or linkage to lipophilic agents and the like which would facilitate the uptake of NM23 by tumor cells, alter the cell specificity of its expression, improve the stability of the expressed gene, and the like. NM23 protein or a portion of the protein could be used for therapy as well, either as is or the protein could be modified to increase its uptake by cells, specificity for target cells (cells to be treated), efficacy or stability and the like. The NM23 protein in a suitable carrier or NM23 DNA with a suitable vector could be injected intravenously or intraperitoneally, administered orally, inhaled, applied to the eyes, introduced into the urinary bladder, applied to the skin or administered by other routes well known to the artisan in the field.

Similar types of strategies can also be used to replace NM23 in tumor cells that have deletions or mutations in NM23. In addition, new cancer therapeutic drugs can be identified on the basis of their stimulation of tumor cell NM23 expression. For example, certain cytokines have been identified, including tumor growth factor beta, which elevate NM23 expression in cancer cells. These and other agents or drugs can be administered to lower the aggressiveness of primary tumors or reduce metastasis. Additionally, proteins or compounds with enzymatic activity similar to NM23 can also be used to achieve the results described herein. Efficacy, specificity or the level of NM23 can be enhanced by conjugating NM23 or a portion thereof with toxins, antibodies, radionucleides, other therapeutic reagents and the like as will be easily suggested to one of ordinary skill in the art. Isolated, substantially pure (as pure as can be obtained by standard isolation and purification techniques) NM23 protein can be synthesized by standard recombinant or chemical technology or the like. A composition comprises an effective amount of the NM23 protein to enhance NM23 level in the cancer cells and a pharmaceutically acceptable carrier.

Somatic cell hybrid analysis of chromosomal localization.

The isolation and characterization of the hybrids has been described (McBride, O. W., *Proc. Nat'l. Acad. Sci. USA* 83:130–134, 1986;

McBride, O. W., *Nucleic Acids Res.* 11:8221–8236, 1982). DNA samples from independent human-mouse and human-hamster somatic cell hybrids and subclones were digested with EcoRI, and the fragments resolved on 0.7% agarose gels. Southern blots were prepared on nylon membranes and hybridized to a random primer labeled 756 bp nm23-H1 CDNA insert (Rosengard, A. M. (1990) *Nature* 342:177–180). Blots were washed at high stringency (<10% divergence) in 0.1×SSC$^3$, 0.2% (w/v) SDS at 55° C. After autoradiography, the presence of the hybridizing human sequences in the DNA samples was correlated with the specific human chromosomes retained in each of the somatic cell hybrids.

In situ hybridization to metaphase chromosomes.

Peripheral blood lymphocytes from a healthy male (46;XY) were cultured for 72 h at 37° C. in RPMI-1640 supplemented with 15% fetal bovine serum, phytohemagglutinin (0.5 µg/ml), and antibodies. Cultures were then synchronized by addition of BudR (100 µg/ml) for 16 h prior to washing and resuspension in fresh medium containing thymidine (2.5 µg/ml) and incubation for an additional 5.5 h (Bhatt, B., *Nucleic Acids Res.* 16:3951–3961, 1988) with colcemid (0.05 µg/ml) present during the final 20 min. The cells were centrifuged, swollen, and fixed. Air dried metaphase spreads were prepared by standard procedures (Harper, M. E. and Saunders, G. F., *Chromosoma* 83:431–439, 1981). After treatment with RNAse A (100 µg/ml) for 1 h at 37° C., the chromosomal DNA was denatured for 3 min in NaOH (0.07N) in ethanol (64%) (Singh, L. et al., *Chromosoma* 60:377–389, 1977; Landegent, J. E. et al., *Nature* 317:175–177, 1985). Radiolabeled probe (specific activity 3.2×10$^7$ cpm/ug) was prepared by nick translation of the pnm23-H1 plasmid DNA with $^3$H-dTTP and $^3$H-dCTP. The probe was mixed with hybridization solution (50% formamide, 5% dextran sulphate, 2X Denhardt's solution, 2X SSC, 5 mM EDTA, 20 mM sodium phosphate, pH 6.4, and 200 µg/ml sheared herring sperm DNA), heat denatured, applied to slides (3×10$^5$ cpm probe/slide), and hybridized for 20 h at 42° C. Slides were washed in 50% formamide-2X SSC (pH 7) for 10 minutes at 42° C. and in 2X SSC at 42° C. to remove the non specifically bound probe and coated with a 50% solution of NTB2 nuclear track emulsion (Kodak, Rochester, N.Y.). The slides were stored desiccated at 4° C. for 9 days and then developed, stained (0.5% Wright stain) and photographed. The slides were destained and chromosomal banding was obtained by staining with 33258 Hoechst (150 µg/ml) for 30 minutes and exposure to UV illumination for 30 minutes after rinsing. The slides were again stained with Wright stain and the same metaphase spreads were rephotographed (Harper, M. E. and Saunders, G. F., *Chromosoma* 83:431–439, 1981).

Gross Structural Alterations.

Genomic DNA was isolated from the normal and tumor tissues of 109 cancer patients by standard methods. DNA was restricted with Bgl II or EcoRI, resolved on 0.8% agarose gels, and Southern blots prepared. Southern blots were hybridized to a random primer labeled 756 bp pNM23-H1 insert (Rosengard, A. M., *Nature* 342:177–180, 198) in 50% (v/v) formamide, 5X SSC, 50 mM Tris-HCl, pH 7.5, 5X Denhardt's solution, 0.5% (w/v) SDS, 250 µg/ml denatured salmon sperm DNA, 0.1% (w/v) Dextran sulfate at 42° C., washed to a final stringency of 0.1×SSC, 0.2% (w/v) SDS, 1 mM EDTA, 65° C., and hybridization detected by autoradiography.

Cancer study.

A prospective colorectal cancer study, initiated in 1988, collected specimens heparinized blood, tumor, and normal tissue from the proximal margin of resection. Patients were evaluated for distant metastasis by monthly serum carcinoembryonic antigen levels, quarterly outpatient visits, and annual colonscopy, chest X-ray, and computerized abdominal and pelvic tomography. Differences in frequency of distant metastasis over time between groups were evaluated by exact log-rank test (Mehta C. R. et al., JASA 83:999–1005, 1988) (StatXact, Cytel Software, Cambridge, Mass.).

Tumor DNA extraction.

Extraction of tumor DNA was facilitated by scalpel dissection based on a 5 mcm hematoxylin-eosin stained cryostat section. DNA was extracted as described (Leone A. et al. (1991) *Cancer Research* 51:2490–2493). Southern hybridization to the nm23-H1 probe or B-globin promoter (Bgl II restriction) and to the YNZ 22.1 probe (Hinf I restriction) was described previously (Leone A. et al. (1991) *Cancer Research* 51:2490–2493).

RNA ("Northern") blotting.

RNA can be isolated from tumor samples by any of a number of standard procedures. For example, refinements of the method of Lehrach (1) can be used. RNA is subjected to denaturing gel electrophoresis and transferred to nitrocellulose or other support matrix. The nm23 mRNA can be detected by hybridization of radioactively or non-radioactively labelled nm23-H1 or nm23-H2. mRNA in the tumor will be reflected by the intensity of hybridization. For comparison, hybridization with control probes for mRNA whose level is constant (e.g., B-actin) allows normalization of results. Detection of low levels of nm23-H1 or nm23-H2 indicates a tumor of high malignant potential.

Nuclease protection assays.

RNA isolated from tumor samples can be analyzed for the content of nm23-H1 or nm23-H2 by its ability for duplexes with a labelled complementary DNA or RNA. Using the whole or part of the nm23-H1 or nm23-H2 nucleotide sequence, plasmids can be generated for the production of nucleic acid probes complementary to the corresponding mRNA. Examples of such vectors are those based on the T7 or SP6 promoter for RNA probes or m13 phage for preparation of DNA probes using oligonucleotide priming. Probes prepared from such vectors will be allowed to hybridize to completion to RNA from tumor samples under conditions of excess of probe. Either RNase can be used to remove molar unhybridized RNA probes or S1 nuclease, or other single-stranded specific DNase, can be used to remove unhybridized DNA probe. These are then subject to denaturing gel electrophoresis and autoradiography. The intensity of bands corresponding to protected probe is a measure of the amount of either nm23-H1 or nm23-H2 from the sample. Inclusion of nuclease protection experiments for mRNAs whose levels do not change will allow normalization of results. Detection of tumors with relatively low levels of nm23-H1 or nm23-H2 indicates tumors of high malignant potential.

In situ hybridization of nm23-H1 or nm23-H2 in tumor sections allow analysis of the quantity of nm23-H1 or H2 mRNA in individual cells of a tumor. Probe complementary to the nm23-H1 or H2 sequence can be prepared as described above and allowed to hybridize to mRNA within thin section of tumor sample (either embedded by standard techniques such as by the use of paraffin, or otherwise preserved). Unhybridized probe can be removed by nuclease. Hybridization can be detected by autoradiography or other methods. The intensity of hybridization reflects the amount of nm23-H1 or H2 mRNA within the cells of the tumor. When tumor cells contain low levels of nm23 they are likely to be highly malignant.

Human nm23 DNA (RNA) may also be used to detect abnormalities of such DNA in human cancer cells to thereby aid in predicting the aggressiveness of the cancer (abnormalities are found in more aggressive cells). Such methods include:

(1) DNA isolated from tumors can be examined for abnormalities of the nm23-H1 or H2 gene by blot hybridization. DNA isolated from normal tissue and tumor tissue can be fragmented by restriction enzymes, subjected to gel electrophoresis transferred to nitrocellulose or other support matrix and the nm23-H1 and H2 genes' fragments detected by hybridization using probes containing all or part of the cDNAs described above or other regions of the nm23-H1 or H2 gene (Southern blot procedure). Differences in hybridization pattern between DNA from normal or tumor cells indicate abnormalities in the nm23-H1 or H2 gene.

(2) Identification of allele loss for the nm23-H1 or H2 genes. Restriction length polymorphisms (RFLP) for each nm23 gene can be identified by Southern blot procedure. An RFLP may be used to identify individual alleles for a gene in patients who are heterozygous for an RFLP. If DNA from normal and tumor cells from a single patient indicates that there is an allelic loss in the tumor DNA for either nm23-H1 or H2, such alteration indicates a tumor of high malignant potential.

(3) Identification of genetic abnormalities within the gene sequence for the nm23-H1 or H2. Nucleotide sequence analysis can be used to determined the gene structure of nm23-H1 or H2 in a tumor sample. The nucleotide sequence of nm23-H1 and H2 defines a normal sequence. Changes from these sequences in the DNA of patients indicates tumors of high metastatic potential.

Human nm23 DNA may be incorporated into a suitable expression vehicle to produce human nm23 protein.

The appropriate DNA sequence may be included in any of a wide variety of vectors or plasmids. Such vectors include chromosomal, nonchromosomal and synthetic DNA sequences; e.g., derivatives of SV40; bacterial plasmids; phage DNA's; yeast plasmids; vectors derived from combinations of plasmids and phage DNAs, viral DNA such as vaccinia, adenovirus, fowl pox, virus, pseudorabies, etc.

The appropriate DNA sequence may be inserted into the vector by a variety of procedures. In general, the DNA sequence is inserted into an appropriate restriction endonuclease site by procedures known in the art. Such procedures and others are deemed to be within the scope of those skilled in the art.

The DNA sequence in the vector is operatively linked to an appropriate expression control sequence(s) (promoter) to direct mRNA synthesis. As representative examples of such promoters, there may be mentioned: LTR or SV40 promoter, the *E. coli* lac or trp, the phage lambda PL promoter and other promoters known to control expression of genes in prokaryotic and eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein. As representative examples of appropriate hosts, there may be mentioned: bacterial cells, such as *E. coli*, *Salmonella typhimurium*, fungal cells, such as yeast; animal cells such as CHO or Bowes melanoma; plant cells, etc. The selection of an appropriate host is deemed to be within the scope of those skilled in the art from the teachings herein.

It is also possible to produce human nm23 protein by conventional peptide chemistry; e.g., by use of a peptide synthesizer and solid phase techniques.

Human nm23 protein can be employed to produce nm23 antibodies.

Antibodies against human nm23 protein may be produced by procedures generally known in the art. For example, polyclonal antibodies may be produced by injecting the protein alone or coupled to a suitable protein into a non-human animal. After an appropriate period, the animal is bled, sera recovered and purified by techniques known in the art. Monoclonal antibodies may be prepared, for example, by the Kohler-Millstein (2) technique involving fusion of an immune B-lymphocyte to myeloma cells. For example, antigen as described above can be injected into mice as described above until a polyclonal antibody response is detected in the mouse's sera. The mouse can be boosted again, its spleen removed and fusion with myeloma conducted according to a variety of methods. The individual surviving hybridoma cells are tested for the secretion of anti-nm23 antibodies first by their ability to bind the immunizing antigen and then by their ability to immunoprecipitate nm23-H1 and H2 from cells. Thus, the antibody elicited in response to human nm23 protein may be either a polyclonal or a monoclonal antibody.

nm23 antibodies can be used to detect tumors which have low levels of nm23 protein and thus an increased ability to metastasize or be malignant. Such antibodies may or may not be purified. The format for such assays include:

(1) Immunohistochemical analysis. Sections of the tumor can be reacted with anti-nm23-H1 or H2 antibodies and immunocomplexes detected by standard and commercial approaches such as peroxidase labelled second antibodies. The density of such immunostaining allows an estimation of the amount of nm23-H1 or H2 produced in the cell.

(2) Solid phase immunoassays. Such assays can be used to quantitatively determine the amount of nm23-H1 and H2 in a soluble extract of a tumor tissue. In such an assay one component either antibody or antigen is fixed to a solid support tumor.

Thus, in accordance with a further aspect of the present invention, there is provided an assay for detection or determination of human nm23 protein which employs nm23 antibody, of the type hereinabove described, as a specific binder in the assay.

The assay technique which is employed is preferably an assay wherein the nm23 antibody is supported on a solid support, as a binder, to bind human nm23 protein present in a sample, with the bound protein then being determined by use of an appropriate tracer.

The tracer is comprised of a ligand labeled with a detectable label. The ligand is one which is immunologically bound by the human nm23 protein and such ligand may be labeled by techniques known in the art.

Thus, for example, the human nm23 protein bound to the nm23 antibody on the solid support may be determined by the use of nm23 antibody which is labeled with an appropriate detectable label.

In such a sandwich assay technique, the labeled nm23 antibody may be a monoclonal antibody or a polyclonal antibody; e.g., the polyclonal antibody may be an antibody which is specific for human nm23 protein which antibody may be produced by procedures known in the art; for example inoculating an appropriate animal with human nm23 protein.

The detectable label may be any of a wide variety of detectable labels, including, enzymes, radioactive labels, chromogens (including both fluorescent and/or absorbing dyes) and the like. The selection of a detectable label is deemed to be within scope of those skilled in the art from teachings herein.

The solid support for the nm23 antibody may be any one of a wide variety of solid supports and the selection of a suitable support is deemed to be within the scope of those skilled in the art from the teachings herein. For example, the solid support may be a microliter plate; a tube, a particle, etc.; however, the scope of the invention is not limited to any representative support. The nm23 antibody may be supported on the support by techniques known in the art; e.g., by coating; covalent coupling, etc. The selection of a suitable technique is deemed to be within the scope of those skilled in the art from the teachings herein.

The sandwich assay may be accomplished by various techniques; e.g., "forward", "reverse"; or "simultaneous"; however, the forward technique is preferred.

In a typical procedure, the nm23 antibody, which is supported on a solid support is initially contacted with a sample containing or suspected of containing human nm23 protein to bind specifically any of such protein present in the sample to such antibody on the support.

After washing of the solid support, the support is contacted with a tracer which binds to human nm23 protein. If such protein is present in the sample, the tracer becomes bound to such protein bound to the antibody on the solid support, and the presence of tracer on the solid support is indicative of the presence of human nm23 protein in the sample. The presence of tracer may be determined by determining the presence of the detectable label by procedures known in the art.

Although the preferred procedure is a sandwich assay, it is to be understood that the nm23 antibody may be used in other assay techniques, e.g., an agglutination assay wherein the nm23 antibody is used on a solid particle such as a latex particle.

EXAMPLE 1

Chromosomal Localization of nm23-H1

The nm23-H1 gene was localized to human chromosome 17 by Southern blot analysis of DNA samples isolated from human-rodent somatic cell hybrids (Table 1). In EcoRI digests, the 21 kb and 4.6 kb (or 2.2 kb and 2.4 kb alleles) hybridizing human sequences segregated concordantly with chromosome 17 and discordantly (greater than 29%) with all other human chromosomes. A 1.7 kb human sequence segregated with chromosome 16 in these hybrids. In a second set of cell hybrids, in which human fibroblasts containing a 17;22 (p13;q11) reciprocal chromosome translocation were fused with Chinese hamster cells (McBride, O. W., Proc. Nat'l. Acad. Sci. USA 83:130–134, 1986), the nm23-H1 gene segregated with the 17p12-qter translocation chromosome and discordantly with the 17p13 band. Thus, the nm23-H1 gene and the p53 tumor suppressor gene at 17p13 (McBride, O. W., Nucleic Acids Res. 11:8221–8236, 1982) were localized to different regions of chromosome 17.

Figure 1A:
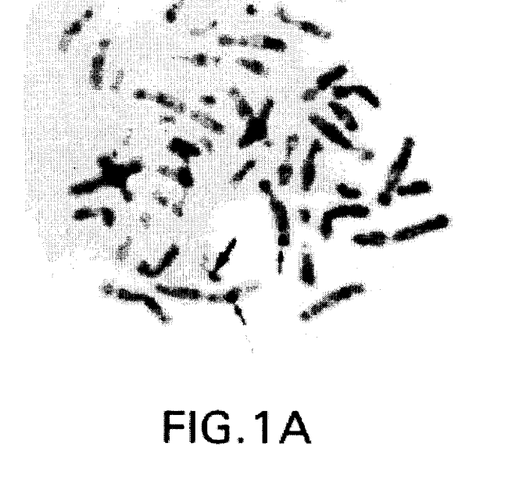
Figure 1B:
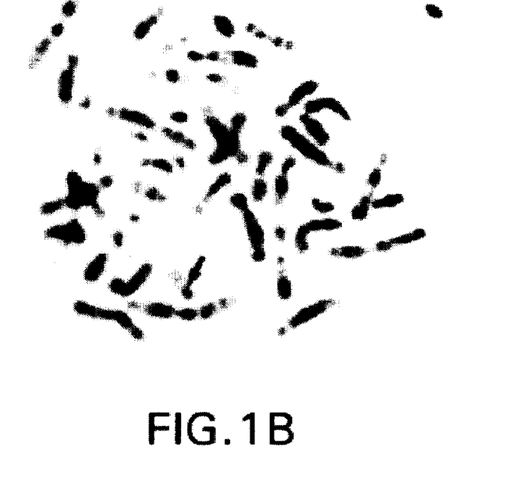
Figure 1C:
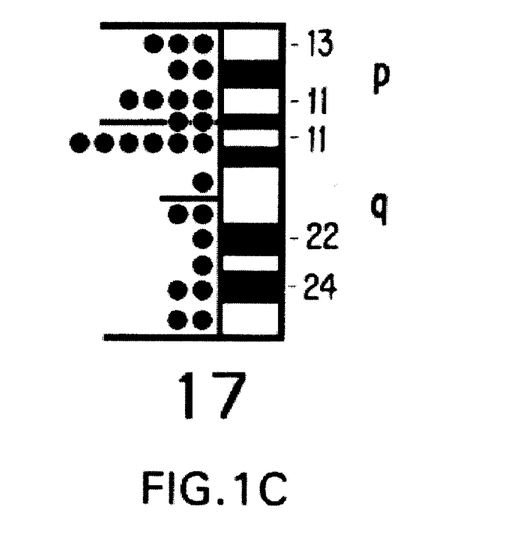

The nm23-H1 gene was further regionally localized to the centromeric region of chromosome 17 (p11-q11) by in situ hybridization to metaphase chromosomes (FIG. 1), and a cross hybridizing sequence on chromosome 16 was also observed.

The functional nm23-H1 gene was definitely assigned to chromosome 17 by two different methods. First, a 200 pb probe prepared from the 3' untranslated sequence from this cDNA identified the 21 kb EcoRI band which segregated with chromosome 17, and detected no sequences on chromosome 16. Second, using both EcoRI and Bgl II polymorphisms for linkage analysis in the 40 C.E.P.H. pedigrees (Dausset, J. et al., Genomics 6:575–577, 1990), a highly significant linkage was observed to the Hox-2 marker assigned to the chromosome 17, which also suggested a regional localization to the proximal portion of the long arm, at 17q21[4].

TABLE 1

Segregation of nm23-H1 gene with human chromosome 17

| Human Chromosome | Gene/Chromosome | | | | & Discordancy |
|---|---|---|---|---|---|
| | +/+ | +/− | −/+ | −/− | |
| 1 | 28 | 26 | 3 | 35 | 32 |
| 2 | 24 | 30 | 2 | 36 | 35 |
| 3 | 22 | 32 | 13 | 25 | 49 |

TABLE 1-continued

Segregation of nm23-H1 gene with human chromosome 17

| Human Chromosome | Gene/Chromosome | | | | % Discordancy |
|---|---|---|---|---|---|
| | +/+ | +/− | −/+ | −/− | |
| 4 | 38 | 16 | 20 | 18 | 39 |
| 5 | 19 | 35 | 6 | 32 | 45 |
| 6 | 31 | 23 | 16 | 22 | 42 |
| 7 | 29 | 25 | 8 | 30 | 36 |
| 8 | 27 | 27 | 9 | 29 | 39 |
| 9 | 23 | 31 | 9 | 29 | 43 |
| 10 | 15 | 39 | 4 | 34 | 47 |
| 11 | 23 | 31 | 4 | 34 | 38 |
| 12 | 31 | 23 | 6 | 32 | 32 |
| 13 | 30 | 24 | 3 | 35 | 29 |
| 14 | 31 | 23 | 10 | 28 | 36 |
| 15 | 30 | 24 | 15 | 23 | 42 |
| 16 | 27 | 27 | 10 | 28 | 40 |
| 17 | 54 | 0 | 0 | 38 | 0 |
| 18 | 35 | 19 | 13 | 25 | 35 |
| 19 | 23 | 31 | 5 | 33 | 39 |
| 20 | 29 | 25 | 11 | 27 | 39 |
| 21 | 37 | 17 | 23 | 15 | 43 |
| 22 | 17 | 37 | 9 | 29 | 50 |
| X | 29 | 25 | 18 | 20 | 47 |

Southern blots of human rodent somatic cell hybrid DNA samples were hybridized to a 756 bp fragment of the pnm23-H1 clone. A 4.6 kb nm23-H1 band was allelic with 2.2 and 2.4 kb bands. A 21 kb non allelic nm23-H1 band was also detected. These bands were readily resolved from 3.2 kb, 5.1 kb, 6.1 kb, 6.9 kb, and 7.9 kb bands or 1.3 kb, 3.5 kb, 4.3 kb, 4.9 kn and 5.8 kb cross-hybridizing bands in Chinese hamster and mouse digests, respectively. Detection of the human bands was correlated with the presence or absence of each human chromosome in the group of somatic cell hybrids. Discordancy represents presence of the gene in the absence of the chromosome (+/−) or absence of the gene despite the presence of the chromosome (−/+), and the sum of these numbers divided by total hybrids examined (x100) represents percent discordancy. The human-hamster hybrids contained 27 primary clones and 13 subclones (16 positive of 40 total) and the human-mouse hybrids represented 16 primary clones and 36 subclones (38 positive of 52 total).

EXAMPLE 2

Somatic Allelic Deletion

Figure 2A:
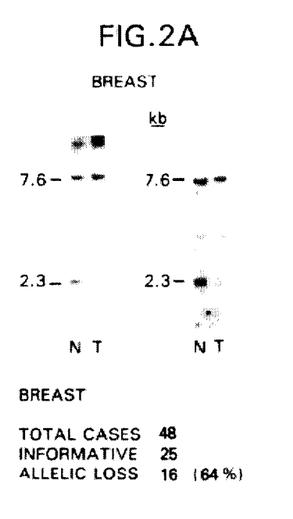
Figure 2B:
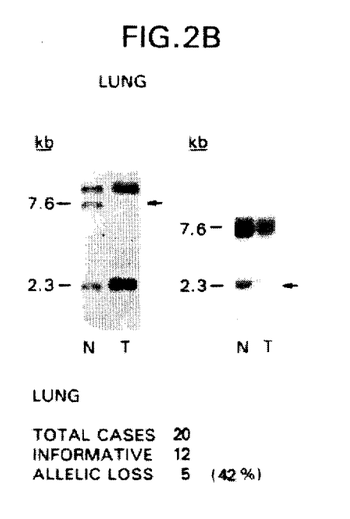
Figure 2C:
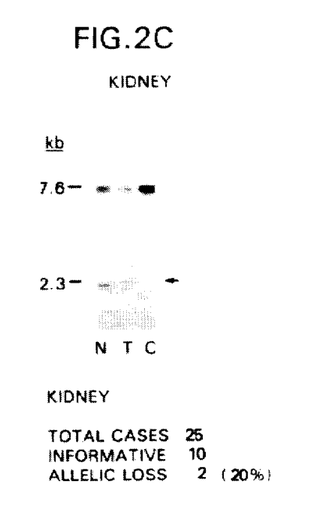
Figure 3A:
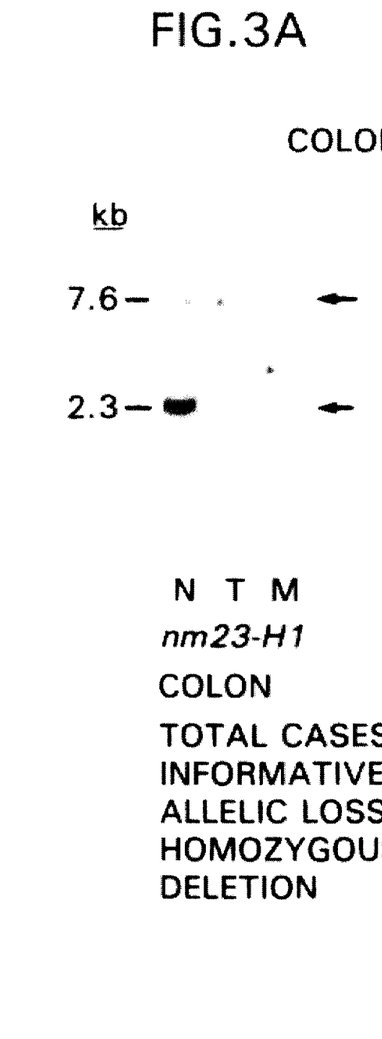

A Bgl II restriction fragment length polymorphism (RFLP) of human chromosomal DNA, which identified nm23-H1 allelic bands at 2.3 and 7.6 kb, was used for analysis of possible nm23-H1 somatic allelic deletion in human carcinomas. A total of 109 paired DNA samples from matched normal tissue and renal, lung, colon or breast carcinomas were analyzed for possible nm23-H1 allelic deletions (FIGS. 2–3). In human breast carcinomas, 64% of informative (heterozygous) tumors exhibited a deletion of one nm23-H1 allele (FIG. 2A). Previous studies with this same cohort of breast tumors analyzed allelic deletion at the transforming growth factor-α (2p13), somatostatin (3p28), MYB (6q22-23) and B platelet derived growth factor (22q12.3-q13.1) loci, and reported a background rate of allelic deletion of less than 7% (Cropp, C. S. et al., Proc. Nat'l. Acad. Sci. USA 87:7737–7741, 1990). In non-small cell lung carcinomas, 42% of informative cases exhibited nm23-H1 allelic deletion (FIG. 2B). All of the lung tumors exhibiting nm23-H1 allelic deletions were adenocarcinomas; Tumors without detectable nm23-H1 allelic deletion included adenocarcinomas, osteosarcomas, squamous cell carcinomas and large cell carcinomas. These data stand in contrast to previous studies in non-small cell lung carcinoma, in which allelic deletions at other chromosome 17 loci were observed primarily in squamous cell carcinomas (Weston, A. et al., Proc. Nat'l. Acad. Sci. USA 86:5099–5103, 1989). Among renal carcinomas from patients with metastatic disease, 20% of informative cases exhibited nm23-H1 allelic deletion (FIG. 2C). A cell line established from each tumor to eliminate normal cell contamination indicated that the small amount of remaining nm23-H1 hybridization to tumor DNA was due to the presence of contaminating normal cells. Finally, among invasive (Duke's C classification) colon carcinomas, 22% of informative cases exhibited nm23-H1 allelic deletions (FIG. 3A, normal and tumor lanes). The data establish that the nm23-H1 gene is subject to somatic allelic deletion in human tumors.

Figure 3B:
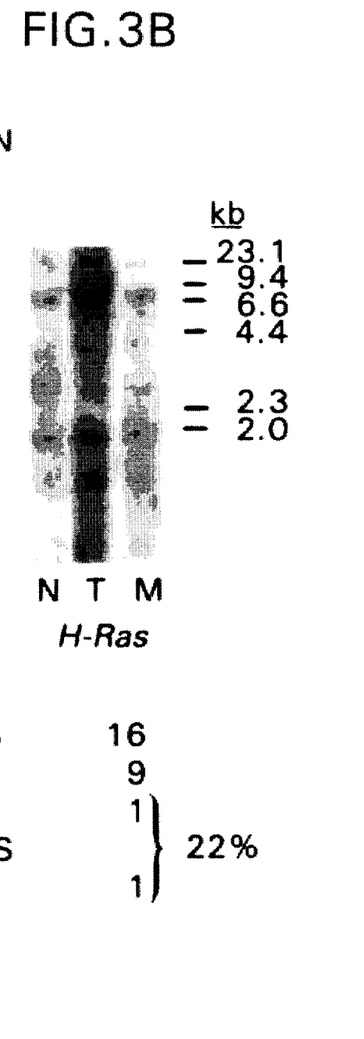

In the colon carcinoma case shown in FIG. 3A, DNA samples from normal colonic mucosa, the primary tumor and a lymph node metastasis were examined. In addition to the allelic deletion in the primary tumor; previously described, a homozygous deletion of nm23-H1 was observed in the lymph node metastasis. Rehybridization of the same filter with a control Ha-ras probe (11p15.5) indicated approximately equivalent amounts of DNA in each lane (FIG. 3B). On a long exposure, a small amount of hybridization to the nm23-H1 bands was observable in the lymph node metastasis DNA, but may result from contaminating normal cells, as was demonstrated in renal carcinoma. The data in this case indicate a sequential series of alterations, from a single allelic deletion to a homozygous deletion, that was correlated with metastatic progression. The normal, primary tumor and lymph node metastasis DNAs from this patient each exhibited bands of hybridization to the p53 suppressor gene on Southern blots, but the case was uninformative for allelic deletion at this locus. Thus, the nm23-H1 homozygous deletion data were not due to the complete deletion of both copies of chromosome 17.

The relative independence of nm23-H1 allelic deletions to allelic deletions at other chromosome 17 loci was determined. The normal/tumor DNA sets were hybridized to at least three other chromosome 17 probes, including p53, (17p13, BglIII digest); YNZ22.1, (17p13.3, BamHI, TaqI or HinfI digests); p144D6 (17p13.3, PstI digest); pHF12.2 (17p12), MspI digest); THH59 (17q23-25.3, PvuII digest). Nine normal/tumor DNA sets were identified that: (a) were informative for both nm23-H1 and another chromosome 17 probe, and (b) exhibited a nm23-H1 allelic deletion. Of these, 2 cases exhibited an nm23-H1 allelic deletion, but was heterozygous at the YNZ 22.1 locus; one case exhibited an nm23-H1 allelic deletion, but was heterozygous at the p53 locus. The data indicate that deletions of relatively large areas of chromosome 17 occur in many tumors, suggesting that nm23-H1 and/or other chromosome 17 genes may be the targets; In 3/9 cases, however, evidence for specificity in nm23-H1 allelic deletion was obtained.

EXAMPLE 3

NM23-H1 Allelic Deletions in Colorectal Carcinoma

Twenty-one patients, clinically free of distant metastases at initial operation were identified as heterozygous at the nm23-H1 allelic deletions of tumor DNA, including 1 patient with a homozygous deletion of both tumor alleles. Rehybridization of membranes with control 5' B-globin probe, which has 1 Bgl II site, revealed comparable loading and adequate digestion of tumor and normal DNA.

The median age was 61 for 11 patients with nm23-H1 allelic deletions of tumor DNA and 70 for 10 patients with no nm23-H1 deletions. No significant difference was observed in location, follow-up time, or TNM stage of patients with nm23-H1 deletions compared to patients who had no nm23-H1 deletions (Table 2). All four patients in whom tumor invaded blood vessels had nm23-H1 deletions. Eight of 11 patients with nm23-H1 deletions developed distant metastases over a median follow-up of 25 months. In contrast, only 2 to 10 patients without nm23-H1 deletions developed distant metastases; both were TNM stage 3 at initial operation. Prevalence of distant metastases was significantly different in patients with nm23-H1 allelic deletions compared to patients with no nm23-H1 deletion ($p<0.03$).

Three patients with nm23-H1 deletions showed no detectable distant metastasis. One patient died of cervical spine dislocation 16 months after operation. Another patient had no evidence of disease 31 months after operation. The remaining patient had no evidence of disease 26 months later, but his tumor displayed vascular invasion, and he may harbor residual disease which has escaped clinical detection.

The 21 paired DNA samples were probed with YNZ 22.1, located near p53. Two of 4 patients with YNZ 22.1 allelic deletions developed distant metastases, while 5 of 11 heterozygous patients without YNZ 22.1 allelic concordant YNZ 22.1 and nm23-H1 allelic deletions; one is alive with distant metastasis and the other has no detectable metastasis.

Eight of 11 patients with nm23-H1 allelic deletions developed distant metastases, including 2 with TNM stage 1 lesions at initial operation (Table 2). In contrast, only 2 of 10 patients in whom nm23-H1 deletions were not detected developed distant metastases ($p<0.03$); no stage 1 or 2 tumor without nm23-H deletion has detectable distant metastasis yet (Table 2). No significant difference in overall survival has emerged yet between the 2 groups.

No significant association was observed between allelic deletion at the YNZ 22.1 locus near p53 and development of distant metastasis in this patient population. Five of 11 heterozygous tumors without nm23-H1 allelic deletions developed distant metastases; 4 of the 5 YNZ 22.1 negative tumors which developed distant metastases displayed nm23-H1 allelic deletions. The distance between nm23-H1 at 17q21 and p53 at 17p13 and different patterns of allelic deletions with nm23-H1 and YNZ 22.1 suggest that the results cannot be explained by deletion of large portions of chromosome 17.

TABLE 2

Clinical Course of Patients with Colorectal Cancer According to nm23-H1 Allelic Deletion and TNM Stage

| TNM Stage | NM23-H1 Delet.[1] | Status[2] | Dist. Mets.[3] | Metas-free Surv[4]. (mos.) | Overall Surv[4]. (mos) |
|---|---|---|---|---|---|
| 1 | y | DOD | y | 11 | 31 |
| 1 | y | AWD | y | 18 | 32 |
| 1 | y | NED | n | 31 | 31 |
| 2 | y | AWD | y | 5 | 25 |
| 2 | y(2) | NED | n | 26 | 26 |
| 2 | y | DOC | n | 16 | 16 |
| 3 | y | AWD | y | 17 | 25 |
| 3 | y | DOD | y | 8 | 25 |
| 3 | y | AWD | y | 6 | 37 |
| 3 | y | AWD | y | 17 | 27 |

TABLE 2-continued

Clinical Course of Patients with Colorectal Cancer According to nm23-H1 Allelic Deletion and TNM Stage

| 3 | y | DOD | y | 3 | 30 |
|---|---|---|---|---|---|

Total with distant metastasis 8/11 (73%)[5]

| TNM Stage | NM23-H1 Delet.[1] | Status[2] | Dist. Mets.[3] | Metas-free Surv[3]. (mos.) | Overall Surv[3]. (mos) |
|---|---|---|---|---|---|
| 1 | n | NED | n | 25 | 25 |
| 1 | n | NED | n | 21 | 21 |
| 2 | n | NED | n | 25 | 25 |
| 2 | n | DOC | n | 6 | 6 |
| 2 | n | NED | n | 23 | 23 |
| 3 | n | DOD | y | 7 | 23 |
| 3 | n | DOD | y | 8 | 12 |
| 3 | n | NED | n | 23 | 23 |
| 3 | n | DOC | n | 5 | 5 |
| 3 | n | NED | n | 26 | 26 |

Total with distant metastasis 2/10 (20%)[5]

Key to Table 2 Abbreviations
[1] Presence of nm23-H1 allelic deletions based on hybridization of pnm23-H1 probe to Bgl II digested genomic DNA (Y = yes, N = no)
[2] Status as of last follow-up exam: AWD, alive with disease; NED, no evidence of disease, DOD, dead of disease; DOC, dead of other causes (cervical spine fracture, respiratory arrest, stroke, respectively).
[3] Dist. mets. = distant metastases detected at operation or radiographically
[4] Metas,-free surv. = Survival without detectable distant metastasis. Overall surv. = Months of alive, regardless of presence or absence of distant metastasis.
[5] Frequency of distant metastasis over time significantly different in patients with nm23-H1 allelic deletions; $p < 0.03$ by exact log-rank test.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method of diagnosing metastatic potential of carcinoma in a human subject who has been identified as having previously had or currently having a carcinoma selected from the group consisting of breast carcinoma, non-small cell lung carcinoma, and kidney carcinoma, said metastatic potential being due to allelic deletions in the human nm23 gene, nm23-H1, said method comprising the steps of:

(a) obtaining a sample of chromosomal DNA from the tumor of a human subject having been identified as having previously had or currently having a tumor said tumor due to a carcinoma selected from the group consisting of breast carcinoma, non-small cell lung carcinoma and kidney carcinoma; and (b) analyzing said sample of chromosomal DNA for the presence or absence of a human nm23-H1 allele said absence of a human nm23-H1 allele being indicative of metastatic potential.

2. A method of diagnosing metastatic potential of colorectal carcinoma in a human subject who has been identified as having previously had or currently having colorectal carcinoma, said metastatic potential being due to homozygous deletions in the human nm23 gene, nm23-H1, said method comprising the steps of:

(a) obtaining a sample of chromosomal DNA from the tumor of a human subject having been identified as having previously had or currently having had a tumor due to colorectal carcinoma; and (b) analyzing said sample of chromosomal DNA for the presence or homozygous deletion of human nm23-H1 said homozygous deletion of human nm23-H1 being indicative of metastatic potential.

3. A method of diagnosing metastatic potential of neuroblastoma in a human subject who has been identified as having previously had or currently having neuroblastoma, said metastatic potential being due to amplification of the human nm23 gene, nm23-H1, the method comprising the steps of:

(a) obtaining a sample of DNA from a tumor of a human subject having been identified as having previously had or currently having a tumor due to neuroblastoma; and (b) analyzing said sample of DNA for amplification of an nm23-H1 allele, said amplification of an nm23-H1 allele being indicative of metastatic potential.

* * * * *